US011064867B2

(12) United States Patent
Frey et al.

(10) Patent No.: US 11,064,867 B2
(45) Date of Patent: Jul. 20, 2021

(54) SHANK INSTRUMENT, IN PARTICULAR A MEDICAL-ENDOSCOPIC SHANK INSTRUMENT

(71) Applicant: RICHARD WOLF GMBH, Knittlingen (DE)

(72) Inventors: Sebastian Frey, Waghäusel (DE); Friedrich Hähnle, Bretten (DE); Eberhard Körner, Knittlingen (DE)

(73) Assignee: RICHARD WOLF GMBH, Knittlingen (DE)

( * ) Notice: Subject to any disclaimer, the term of this patent is extended or adjusted under 35 U.S.C. 154(b) by 374 days.

(21) Appl. No.: 15/757,075

(22) PCT Filed: Aug. 29, 2016

(86) PCT No.: PCT/DE2016/200402
§ 371 (c)(1),
(2) Date: Mar. 2, 2018

(87) PCT Pub. No.: WO2017/036479
PCT Pub. Date: Mar. 9, 2017

(65) Prior Publication Data
US 2018/0256012 A1    Sep. 13, 2018

(30) Foreign Application Priority Data
Sep. 3, 2015   (DE) .................... 10 2015 216 864.6

(51) Int. Cl.
*A61B 1/05*   (2006.01)
*A61B 1/018*  (2006.01)
(Continued)

(52) U.S. Cl.
CPC ...... *A61B 1/00096* (2013.01); *A61B 1/00183* (2013.01); *A61B 1/05* (2013.01); *A61B 1/0684* (2013.01); *A61B 1/018* (2013.01)

(58) Field of Classification Search
CPC ............ A61B 1/00101; A61B 1/00103; A61B 1/00105; A61B 1/00121; A61B 1/00124;
(Continued)

(56) References Cited

U.S. PATENT DOCUMENTS 5,166,787 A     11/1992   Irion
5,707,344 A *   1/1998    Nakazawa ........... A61B 1/0008
                                                     600/107
(Continued)

FOREIGN PATENT DOCUMENTS

EP        1825803 A1 *  8/2007  ......... A61B 1/00089
EP        2 123 225 A1  11/2009
(Continued)

*Primary Examiner* — John P Leubecker
*Assistant Examiner* — Shankar Raj Ghimire
(74) *Attorney, Agent, or Firm* — McGlew and Tuttle, P.C.

(57) ABSTRACT

A medical-endoscopic shank instrument includes a hollow shank (2), a distal side housing (8) in the hollow shank, an electronic picture sensor (14) and/or a light located in the housing. The housing is linearly movable to move the picture sensor and/or the light from within an inner lumen (22) of the hollow shank to outside the inner lumen. The housing is displaceable through an opening (20) formed on a peripheral wall of the hollow shank. An inner-lying outer side (26), opposite and away from the opening, is formed on a peripheral wall of the hollow shank and is supported on an elongate carrier (32) which is guided in the hollow shank. The elongate carrier (32) is configured elastically resiliently transverse to longitudinal extensions thereof and extends essentially over a whole length of the hollow shank and is fixed in a region of the proximal end/proximally of the hollow shank.

9 Claims, 7 Drawing Sheets

(51) Int. Cl.
*A61B 1/00* (2006.01)
*A61B 1/06* (2006.01)

(58) Field of Classification Search
CPC ............ A61B 1/00131; A61B 1/00135; A61B 1/0014; A61B 1/00096; A61B 1/00183; A61B 1/05; A61B 1/0684; A61B 1/018; A61B 1/00128; A61B 1/00137; A61B 1/00147
See application file for complete search history.

(56) References Cited

U.S. PATENT DOCUMENTS

| | | | |
|---|---|---|---|
| 7,066,879 B2* | 6/2006 | Fowler | A61B 1/00149 600/102 |
| 8,403,826 B1 | 3/2013 | Zobel | |
| 9,084,621 B2* | 7/2015 | Weitzner | A61B 1/04 |
| 2002/0049367 A1 | 4/2002 | Irion et al. | |
| 2005/0033115 A1* | 2/2005 | Okada | A61B 1/00101 600/104 |
| 2007/0287992 A1* | 12/2007 | Diolaiti | A61B 34/37 606/1 |
| 2008/0108869 A1 | 5/2008 | Sanders et al. | |
| 2008/0214895 A1* | 9/2008 | Campos | A61B 1/00089 600/129 |
| 2009/0292164 A1* | 11/2009 | Yamatani | A61B 1/018 600/106 |
| 2010/0238279 A1* | 9/2010 | Thoms | A61B 1/247 348/77 |
| 2012/0046524 A1* | 2/2012 | Miyamoto | A61B 1/00091 600/157 |
| 2013/0231531 A1* | 9/2013 | Naito | A61B 1/00064 600/109 |
| 2015/0182239 A1* | 7/2015 | Baker | A61B 17/12009 600/104 |
| 2015/0230697 A1* | 8/2015 | Phee | A61B 1/05 600/106 |
| 2017/0112361 A1* | 4/2017 | Surti | A61B 1/00101 |

FOREIGN PATENT DOCUMENTS

| | | | |
|---|---|---|---|
| JP | 2002065597 A | 3/2002 | |
| JP | 2010506669 A | 3/2010 | |
| JP | 2012200597 A | 10/2012 | |
| WO | 2008/048688 A2 | 4/2008 | |
| WO | WO-2012016224 A2 * | 2/2012 | ......... A61B 1/00089 |

* cited by examiner

SHANK INSTRUMENT, IN PARTICULAR A MEDICAL-ENDOSCOPIC SHANK INSTRUMENT

CROSS REFERENCE TO RELATED APPLICATIONS

This application is a United States National Phase Application of International Application PCT/DE2016/200402, filed Aug. 29, 2016, and claims the benefit of priority under 35 U.S.C. § 119 of German Application 10 2015 216 864.6, filed Sep. 3, 2015, the entire contents of which are incorporated herein by reference.

FIELD OF THE INVENTION

The invention relates to a shank instrument and in particular to a medical-endoscopic shank instrument.

BACKGROUND OF THE INVENTION

Rigid, semi-flexible or flexible shank instruments which are inserted through a natural or artificially created feed channel into the inside of the body of a patient to be treated and used there for examining cavities or hollow organs are applied as standard in the field of minimal invasive surgery. Instruments of this type are also used in the technical field as so-called technoscopes, where they can be applied in difficultly accessible cavities of technical objects.

These shank instruments comprise an observation device and an illumination device for illuminating the observation region, for optically assessing a cavity or a hollow organ. Either lens systems which extend through the shank from the distal end of the shank and are connected to oculars at the proximal side of the shank or electronic picture sensors of a video camera which are arranged at the distal end of the shank are applied as observation devices, wherein the picture sensors are connected to a picture data processing device which is arranged at the proximal side of the shank and to an viewing device which is arranged subsequently to this device. The illumination devices either comprise at least one fibre optic which is led through the shank and is connected to a light source proximally of the shank or comprise at least one light-emitting semiconductor element which is arranged at the distal end of the shank and is connected to a voltage source which is arranged at the proximal side of the shank.

Such shank instruments form the basis of the invention and these, apart from an optical observation, also permit operations in the observation region to be carried out. Concerning these shank instruments, auxiliary instruments such as for example forceps or cutting instruments are led through the shank which is configured as a hollow shank, to the region of operation. Hereby, the free space which is available at the distal end of the shank in the shank laterally next to the parts of the observation and illumination device which are arranged there predominantly determines the type of auxiliary instruments which can be used, since the dimensions of these must correspond to the free space which exists in the shank. Specifically, this means that auxiliary instruments, whose radial dimensions in their region which is led through the shank exceed a certain size, cannot be used. Although there exists the possibility of counteracting this restriction by way of the provision of a hollow shank with a greater diameter, this measure however leads to a significantly increased traumatiation of body tissue having to be possibly accepted in the case of medical-endoscopically applied shank instruments and the application range of the shank instruments generally being restricted due to it not being able to be used at all in body cavities or hollow organs which can only be reached via a very narrow access on account of the size of its shank diameter.

Although from EP 2123225 A1 it is counted as belonging to the state of the art to extend a camera housing which is arranged in the region of the distal shank end out of the inner lumen of the shank, this however is exclusively for optical reasons, in order to obtain an observation position which is more favorable for the operation. The operating channel however is not affected by this and the extending mechanism is complicated, delicate and takes up space.

From U.S. Pat. No. 5,166,787 A, it is counted as belonging to the state of the art to pivotably arrange a camera housing at the distal shank end. This arrangement, although creating a free space in the operating channel, is however critical with regard to the actuation mechanism and leading of cables.

SUMMARY OF THE INVENTION

Against this background, it is an object of the invention to provide a shank instrument and in particular a medical-endoscopic shank instrument which does not have the disadvantages which are described above.

This object is achieved by a shank instrument according to the invention, which is preferably a medical-endoscopic shank instrument, but can also be a technoscope which is applied in the technical field. The shank instrument is provided with a hollow shank, through which, when required, an auxiliary instrument and/or a fluid can be led to the distal side of the hollow shank. The hollow shank can be configured in a rigid as well as, at least in sections, flexibly bendable manner in the direction transverse to it longitudinal extension.

The shank instrument moreover comprises at least one electronic picture sensor and light means, wherein the at last one picture sensor serves for optically capturing a region which is located distally of the hollow shank and the light means are envisaged for illuminating this region which is captured by the picture sensor. All known electronic picture sensors can be used as picture sensors, wherein picture sensors which are configured as semiconductor chips, such as for example CMOS sensors or CCD sensors are preferred on account of their reduced construction size. Light-emitting semiconductor elements such as light diodes or laser diodes are preferably provided as light means, and these are likewise characterized by their reduced construction size.

Concerning the shank instrument according to the invention, the at least one picture sensor and/or the light means are arranged in a housing which is integrated in the hollow shank at the distal side, wherein amongst other things, the term "housing" according to the invention is to be understood as all envelopes which surround the picture sensor or the light means at the outer side, thus also simple coatings. Proceeding from the housing, a picture sensor which is arranged therein is signal-connected to a picture data processing device which is preferably arranged at the proximal side of the hollow shank and in turn is signal-connected to a viewing device. The light means which are provided for illumination are conductively connected to a voltage source which is likewise arranged at the proximal side of the hollow shank, via current leads which are led through the hollow shank. Preferably, a picture sensor as well as at least one light-emitting semiconductor element as a light means, is arranged in a common housing.

The shank instrument according to the invention is characterized in that the housing with the picture sensor which is arranged therein and/or with the light means which are arranged therein is movable in a straight line from a position, in which the picture sensor and/or the light means are arranged within the inner lumen of the hollow shank, which is to say within its clearance profile, into a position, in which the picture sensor and/or the light means are arranged outside the inner lumen of the hollow shank.

An inner lumen in the context of the invention is to be understood as the volume which is enclosed by the shank, thus the volume which is defined by its inner contour.

The shank instrument can therefore have a first operating condition, in which the housing is arranged completely within the outer profile of the hollow shank, and from there can be brought into a second operating condition, in which the housing for the most part is arranged laterally outside the hollow shank, by way of a linear displacement of the housing. In its first operating condition, the hollow shank of the shank instrument can be brought via comparatively narrow feed channels to its designated location in a hollow organ or a cavity, wherein the region distally of the hollow shank can be observed and/or illuminated by way of the picture seniors and/or the light means which are then arranged within the inner lumen of the hollow shank. The housing can subsequently be moved to the greatest possible extent out of the inner lumen of the hollow shank in a straight-lined movement preferably in the radial direction of the hollow shank but possibly also obliquely to the longitudinal extension of the hollow shank, wherein an observation and/or illumination of the region distally of the hollow shank is then also ensured, and particularly advantageously the free space for leading an auxiliary instrument or a fluid through the hollow shank is significantly increased. The variety of auxiliary instruments which can be used in combination with the shank instrument is significantly increased by way of this and possibility of reducing the radial dimensions of the hollow shank of the shank instrument without restricting the variety of the auxiliary instruments which could be applied until now is also opened up. The straight-lined movability of the housing is advantageous inasmuch as this is simple with regard to design and manufacturing and leads to the picture sensor and/or the light means always being aligned equally, which is to say without an angle change with respect to the middle axis of the hollow shank, in the first as well as second operating condition of the shank instrument.

An opening, through which the housing can be displaced is formed on the peripheral wall of the hollow shank, in order to move the housing from a position which is integrated in the hollow shank into a position, in which the housing is arranged largely radially outside the hollow shank. The position and dimensions of this opening hereby usefully correspond to the position and the dimensions of the housing as well as possibly the movement path of the housing, wherein only a small play exists between the housing and the opening, so that the housing and the hollow shank form an as compact as possible unit.

Herein, according to the invention, the housing at its outer side which is opposite and away from the opening which is formed on the peripheral wall of the hollow shank is supported on at least one elongate carrier which is led in the hollow shank, extends essentially over the complete length of the hollow shank and is fixed in the region of the proximal end of the hollow shank or at the proximal side of the hollow shank. The carrier can usefully be fixed in the region of the proximal end of the hollow shank at an as large as possible radial distance to the middle axis of the hollow shank, in order to provide an as large as possible free space in the inner lumen of the hollow shank for leading an auxiliary instrument through the hollow shank.

Herein, the carrier is configured in an elastically resilient manner, so that the carrier, given the action of a corresponding external force, is bendable in the direction transverse to its longitudinal extension and assumes its original shape again after the cessation of this force. This elastically resilient behavior of the carrier is particularly useful since the carrier is fixedly connected to the housing and in this manner can follow a movement of the housing from within the inner lumen of the hollow shank to outside the inner lumen and vice versa, without becoming damaged.

In this context, it has also been found to be advantageous if, as is envisaged according to a preferred further development of the invention, an outer-lying outer side of the housing is aligned in a flush manner with the outer side of the peripheral wall of the hollow shank in the position of the housing within the inner lumen of the hollow shank. Accordingly, the position of the housing which is arranged within the inner lumen of the hollow shank and the contour of the outer-lying outer side of the housing are preferably selected such that the housing which is arranged within the inner lumen of the hollow shank forms a common closed surface with the hollow shank.

According to an advantageous further development of the invention, one envisages a recess which runs in the longitudinal direction of the hollow shank and into which the carrier engages being formed on this inner-lying outer side of the housing which is away from the opening which is formed on the peripheral wall of the hollow shank. The aim of this measure lies in the carrier, given a housing which is moved out of the inner lumen of the hollow shank, having as little effect as possible or no effect at all upon the size of the then created enlarged free space for leading through an auxiliary instrument. For this, the recess is usefully dimensioned such that the carrier does not project out of the housing in the cross-sectional plane of the hollow shank.

The carrier is preferably formed by a flat tube. With regard to an elastic bendability of the carrier transversely to its longitudinal extension, the flat tube is usefully aligned in a manner such that the housing supports itself on a flat side of the flat tube. Hereby, the flat side of the flat tube is aligned normally to the movement direction of the housing. Although the cross-sectional shape of the flat tube which is used as a carrier is generally arbitrary as long as has larger dimensions in a certain cross-sectional direction than in a cross-sectional direction which is aligned normally to this, it is however advantageous if the flat tube has a kidney-shaped cross section. Hereby, the housing for the picture sensor and/or the light means preferably supports itself on a convexly arched flat side of the flat tube whose arching corresponds to the inner cross-sectional contour of the hollow shank, so that the flat tube at least in its distal end section comes to bear on the inner periphery of the hollow shank given a housing which is moved out of the inner lumen of the hollow shank and in this manner affects the free space within the hollow shank, necessary for leading through the instrument, as little as possible. The concavely arched flat side of the kidney-shaped flat tube is hereby opposite and away from the opening which is formed on the peripheral wall of the hollow shank, and this, within the hollow shank, likewise has a positive effect with regard to an as large as possible free space for the auxiliary instruments which are led through the hollow shank, since these auxiliary instruments as a rule have a shank with a circular cross section.

Further advantageously, the connection leads which are connected to the picture sensor and/or to the light diode are led through the flat tube to the proximal side of the hollow shank. Hereby, the flat tube is usefully configured in a closed manner at its distal end, so that the electrical connection leads are shielded completely from a fluid which is possibly led through the free inner lumen of the hollow shank. In the case of several connection leads which are led through the flat tube, these are usefully led at an as large as possible distance to one another, thus distanced to one another in the direction of the largest cross-sectional width of the flat tube. Moreover, additional light means which effect a particularly bright illumination of the region which is captured by the picture sensor can be arranged in the flat tube at its distal end.

The housing is advantageously coupled in movement to a push-pull element which is movable in the hollow shank in the longitudinal direction of the hollow shank, via a cam guide, for the movement control of the housing for the picture sensor and/or the light means, which is to say for controlling the straight-lined movement of the housing from a position, in which the picture sensor and/or the light means are arranged within the inner lumen of the hollow shank, into a position, in which the picture sensor and/or the light means are arranged outside the inner lumen of the hollow shank. Hereby, a movement of the push-pull element which at the proximal side of the hollow shank is actively connected to an actuation device, in the longitudinal direction of the hollow shank, is converted into a movement of the housing transverse to the longitudinal direction of the hollow shank via a cam guide.

For forming the cam guide, the push-pull element preferably comprises at least one projection which is aligned transversely to its movement direction and which engages into a guide groove which is formed on an outer side of the housing and which runs obliquely in the radial direction. If the push-pull element is moved in the longitudinal direction of the hollow shank, then the guide groove which runs obliquely on its outer side and the projection of the push-pull element which engages therein effect a positively guided movement of the housing in the radial direction transverse to the longitudinal extension of the hollow shank or transversely to the movement direction of the push-pull element.

Basically, any elongate component which is suited for force transmission in its longitudinal direction is can be used as a push-pull element. It is particularly with regard to the provision of an as large as possible free space for leading an auxiliary instrument through the hollow shank that it has however been found to be advantages if the push-pull element is formed by a tube which is usefully configured in an as thin-walled as possible manner and has an outer diameter which corresponds to the inner diameter of the hollow shank. In this case, the auxiliary instrument is led through the tube which is arranged in the hollow shank, through the hollow shank. A longitudinal slot, in which the housing for the picture sensor and/or the light means engages, is usefully arranged on the tube which forms the push-pull element. A projection is moreover formed on each of the two longitudinal sides of the longitudinal slot. These two projections which are formed on the longitudinal sides of the longitudinal slot engage into two guide grooves which are formed on two outer sides of the housing which are opposite and away from one another.

The invention is hereinafter explained in more detail by way of embodiment examples which are represented in the drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Referring to the drawings, the shank instruments which are represented in the drawing each comprise a hollow shank 2 which is formed by a rigid tube and to which a housing part 4 connects at the proximal side of the hollow shank 2. A housing 8 is integrated in the hollow shank 2 in the region of the distal end 6 of the hollow shank 2. A recess 12, in which a picture sensor 14 is arranged, is formed at a distal face side 10 of the housing 8. Two further recesses 16, in which a light diode 18 is arranged as a light means (as a light) are formed on the face side 10 of the housing 8, laterally of the recess 12. The picture sensor 14 and the light diode 18 are arranged in the housing 8 in an exchangeable manner, so that the picture sensor 14 and the light diodes 18 can be disassembled from the housing 18 when required and can be replaced by another picture sensor 14 or by other light diodes 18.

The housing 8 can be brought through an opening 20 which is formed on the peripheral wall of the hollow shank 2, from a position, in which the picture sensor 24 and the light diodes 8 are arranged within the inner lumen 22 of the hollow shank 2 (FIGS. 1, 3 and 5) into a position, in which the picture sensor 14 and the light diodes 18 are arranged outside the inner lumen 22 of the hollow shank 2 (FIGS. 2, 4, 6 and 7). An outer-lying outer side 24 of the housing 8, which comprises an arching portion, which is complementary to the outer rounding of the hollow shank 2, is aligned with the outer side of the hollow shank 2 in the position, in which the picture sensor 14 and the light diodes 18 are arranged within the inner lumen 22 of the hollow shank 2.

Figure 5:
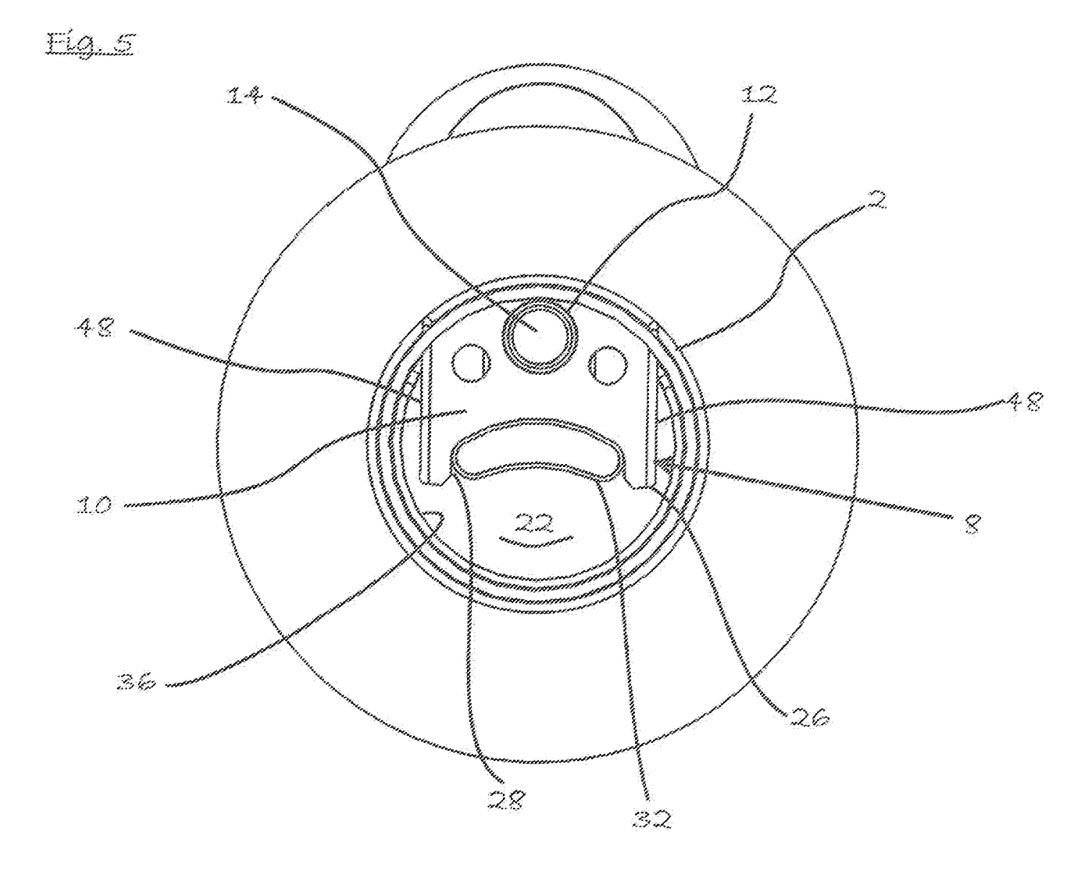
FIG. 5 is a front view of the distal end section of the shank instrument according to FIG. 1, in the first operating condition.
Figure 6:
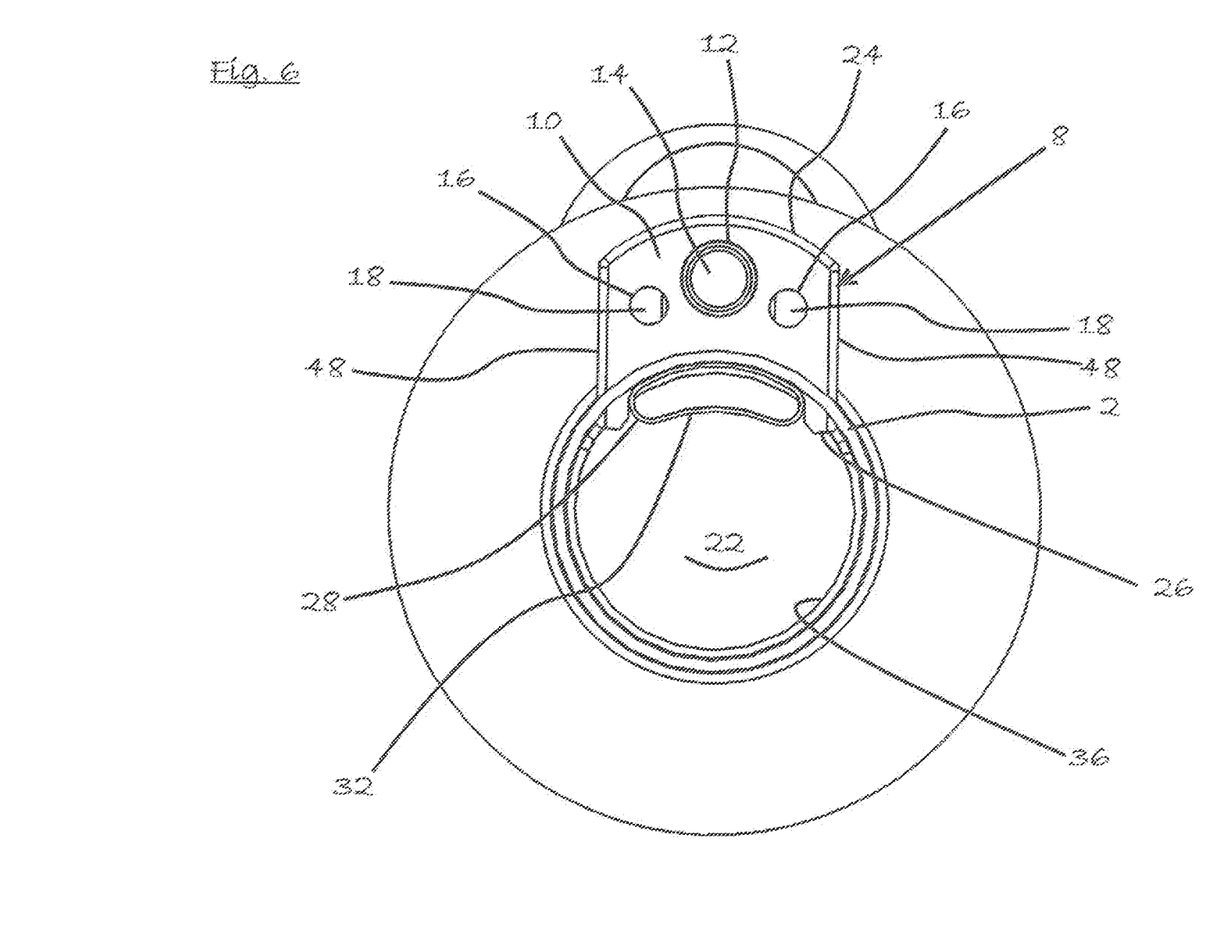
FIG. 6 is a front view, the distal end section of the shank instrument according to FIG. 1 in the second operating condition.

As is particularly clear from FIGS. 5 and 6, a recess 28 is formed on an inner-lying outer side 26 of the housing 8 which outer side 26 is away from the opening 20 or from the outer side 24 of the housing 8. This recess 28 extends in the longitudinal direction of the hollow shank 2 from the distal face side 10 to a proximal face side 30 of the housing 8 and serves for receiving a flat tube 32 with a kidney-shaped cross section. The flat tube 32 extends from the distal end of the hollow shank 2 to the proximal side of the hollow shank 2 and is immovably fixed to the housing part 40 at the proximal side of the hollow shank 2. The flat tube 32 forms a carrier (support), on which the housing 8 is supported in the housing position within the inner lumen 22 of the hollow shank 2 as well as in the housing position moved out of the inner lumen 22. The flat tube 32 has a certain elasticity in a direction transverse to a flat tube longitudinal extension, so that the flat tube 32 can be elastically bent transversely to the flat tube longitudinal extension, in order to be able to follow the movement of the housing 8.

Figure 7:
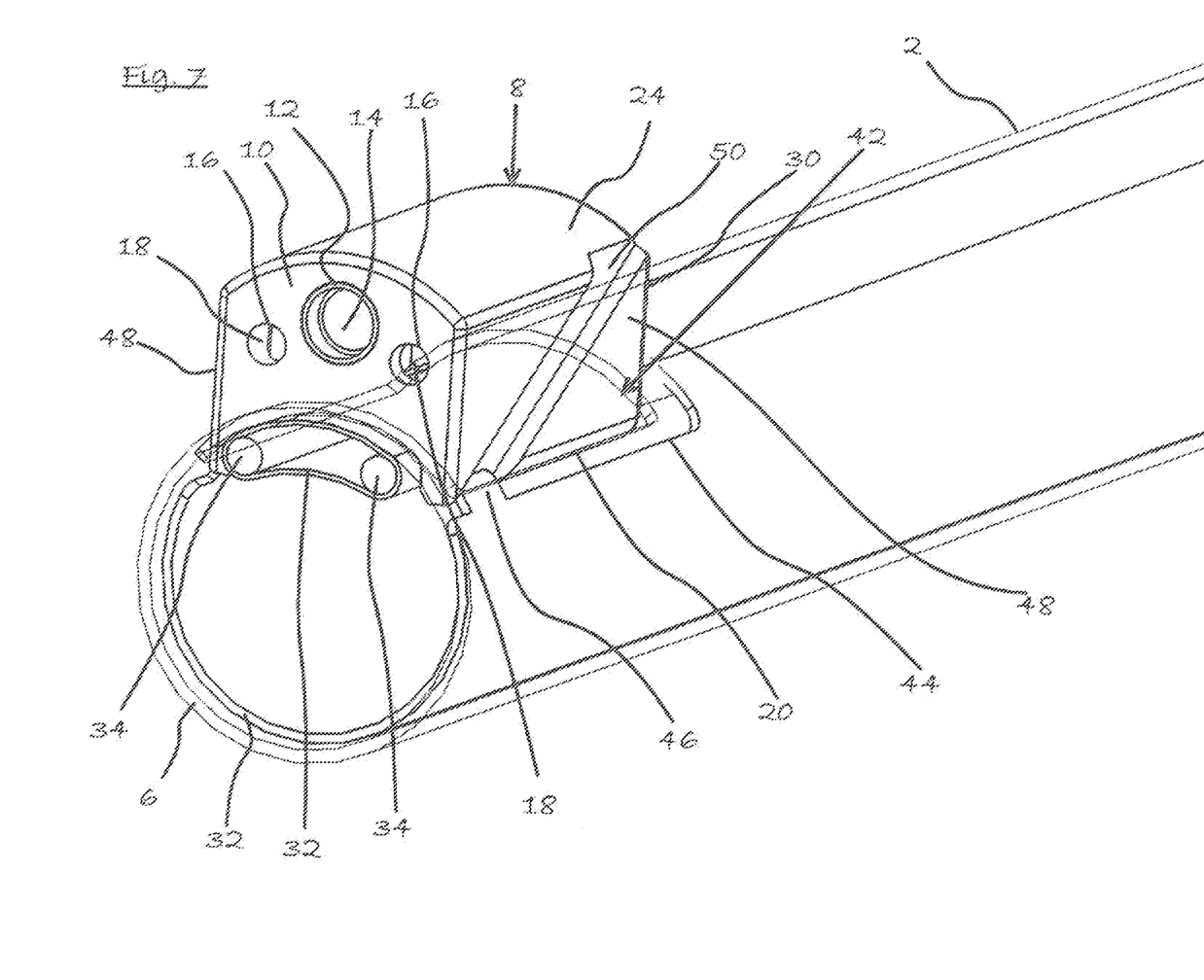
FIG. 7 is an enlarged representation, a distal end region of a shank of the shank instrument according to a second embodiment in a second operating condition.

Apart from a function of the flat tube 32 as a carrier for the housing 8, the flat tube 32 also serves as a guide channel for connection leads which are connected to the picture sensor 14 and to the light diodes 18, but which are not represented in the drawing for a better overview and which are led through the flat tube 32 to a housing part 52 which is arranged at the proximal side of the housing part 4. The connection lead which is connected to the picture sensor 14 is connected at the proximal side of the housing part 52 to a picture data processing device which is not represented. The connection leads which are connected to the light diodes 18 are connected, at the proximal side of the housing part 52, to a voltage source which is likewise not represented. Concerning the embodiment example which is represented in FIG. 7, the flat tube 32 moreover serves for arranging two additional light diodes 34 which effect a particularly bright illumination of a region which is captured by the picture sensor 14 at the distal side of the hollow shank 2. The use of the additional light diodes 34 moreover represents the single difference between the shank instrument which is represented in FIG. 7 and the shank instrument which is represented in FIG. 1-6. Moreover, it should be noted that tubes for leading a rinsing fluid can be applied in the flat tube 32 where the light diodes 34 are arranged, instead of the light diodes 34, by which means a continuous flow rinsing would be possible.

Figure 1:
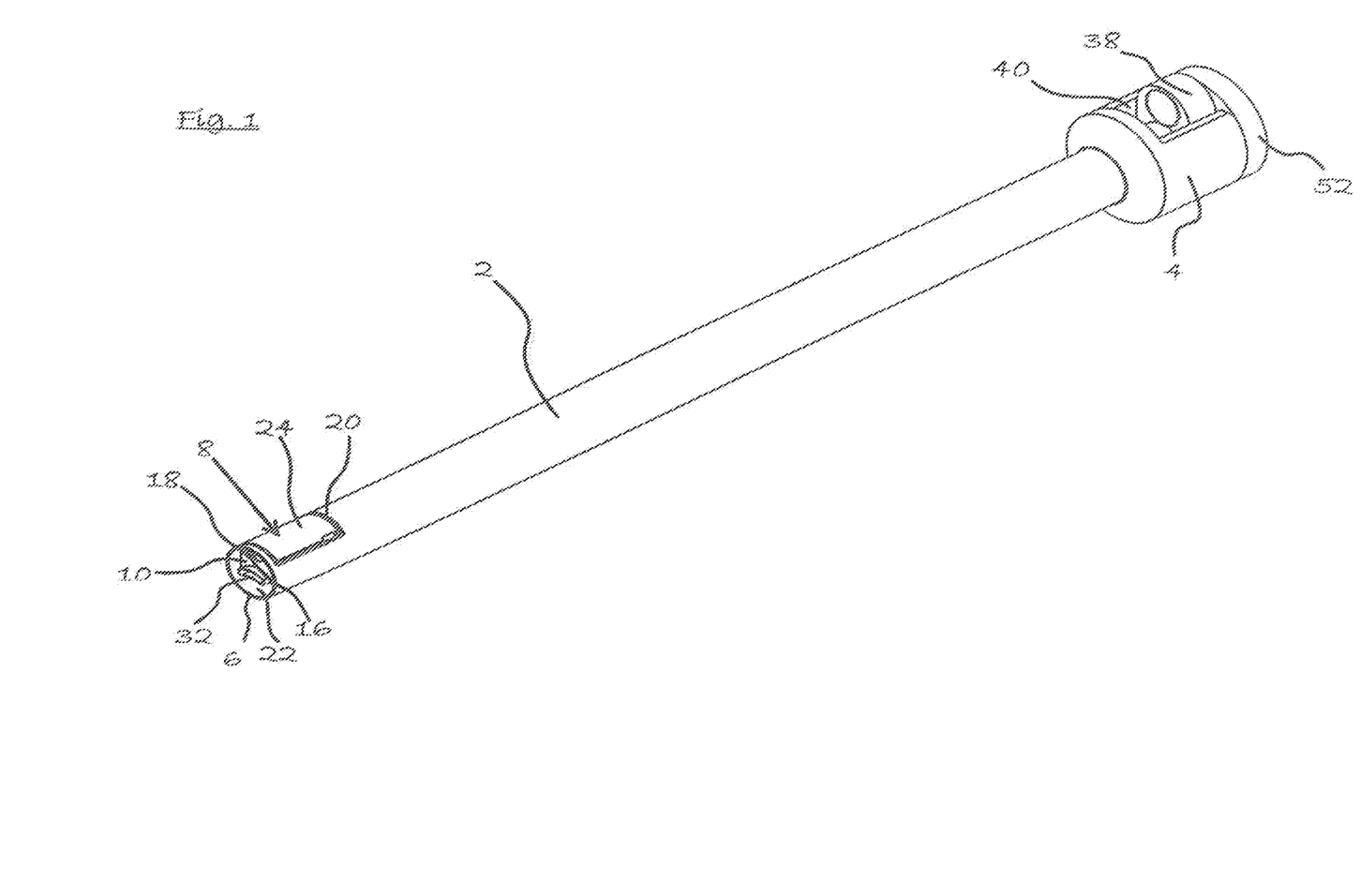
FIG. 1 is a perspective representation of a distal end section of a medical-endoscopic shank instrument in a first operating condition.
Figure 2:
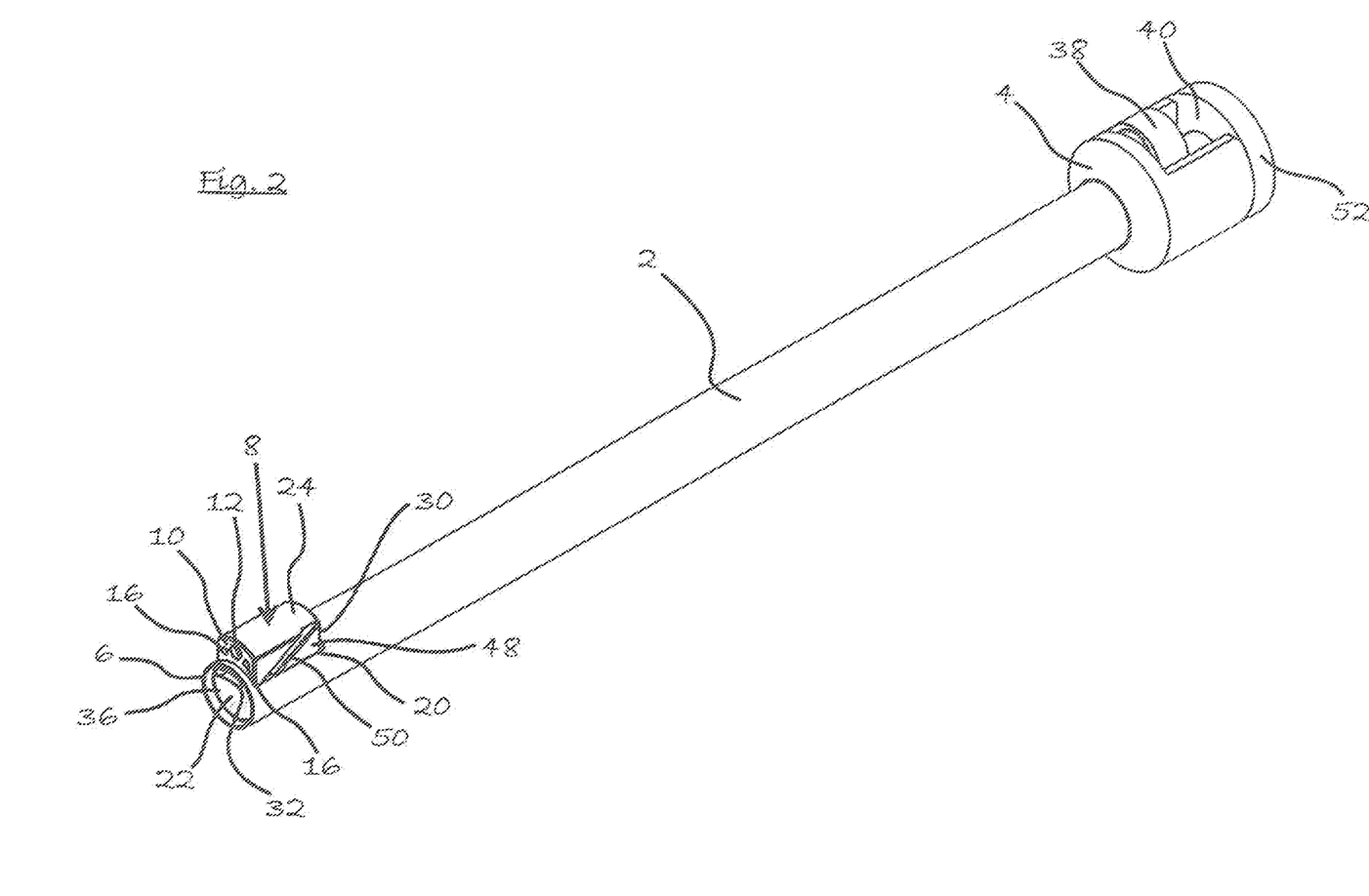
FIG. 2 is a representation according to FIG. 1, with the shank instrument in a second operating condition.
Figure 3:
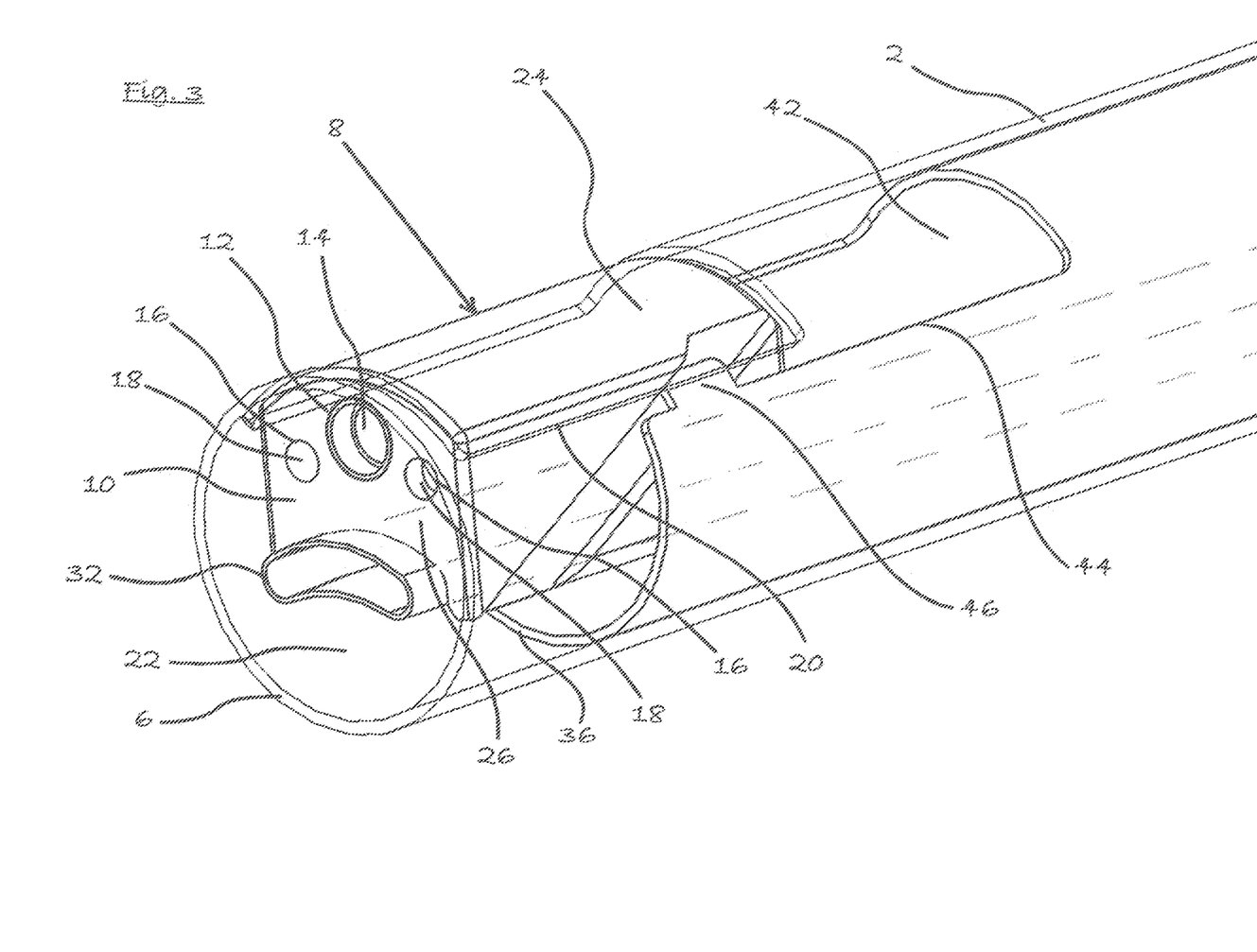
FIG. 3 is an enlarged representation of a distal end region of a shank of the shank instrument according to FIG. 1, in the first operating condition.
Figure 4:
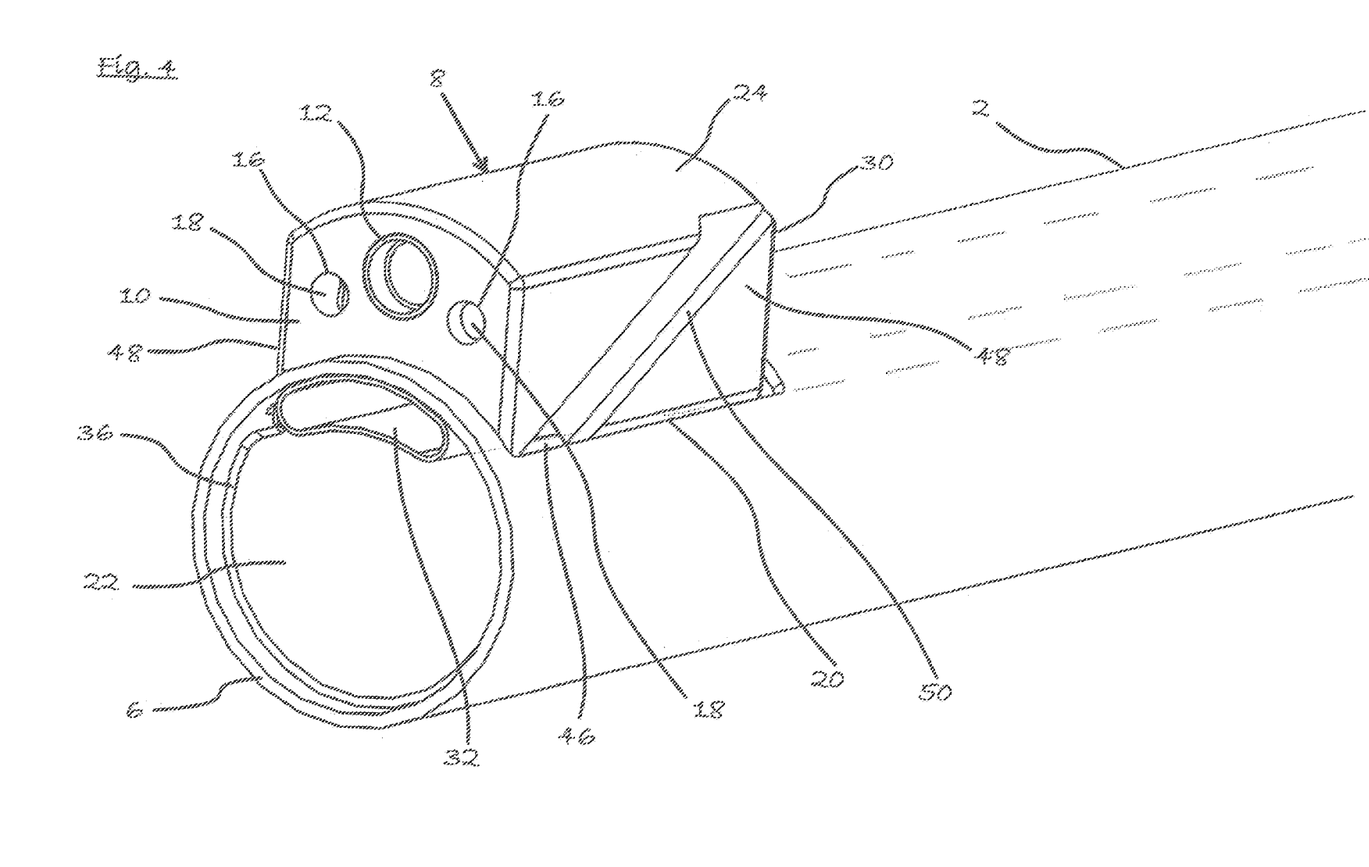
FIG. 4 is an enlarged representation of a distal end region of the shank of the shank instrument according to FIG. 1, in the second operating condition.

A tube 36 which extends to into the housing part 52 is arranged in the hollow shank 2. The tube 36 is displaceable in the hollow shank 2 in the longitudinal direction of the hollow shank 2 and in this manner forms a push-pull element. A slider 38 is fixedly connected to the tube 36 and projects radially on the outer periphery of the tube 36 and engages through an opening 40 which is formed peripherally on the housing part 4. The slider 38 is arranged on the proximal end section of the tube which engages into the housing part 4, for the movement control of the tube 36. The opening 40 is dimensioned such that it permits a limited displacement of the slider 38 in the opening 40 (FIGS. 1 and 2).

The tube 36 serves as an actuation element, with which the housing 8 can be brought via a cam guide from a position, in which the picture sensor 14 and the light diodes 18 are arranged within the inner lumen 22 of the hollow shank 2, into a position, in which the picture sensor 14 and the light diodes 18 are arranged outside the inner lumen 22 of the hollow shank 2. A longitudinal slot 42 which extends in the proximal direction of the tube 36 to a limited extent (FIGS. 3 and 7) is formed on the tube 36 in a manner departing from the distal end of this, for forming the cam guide. The width of the longitudinal slot 42 is dimensioned such that the housing 8 can pass through the longitudinal slot 42 with small play. A projection 46 which projects transversely to the longitudinal extension of the longitudinal slot 42 is formed on the longitudinal sides 44 of the longitudinal slot 42 which are arranged lying opposite one another and run in the axial direction of the longitudinal slot 42. The two projections 46 form sliding blocks which engage in slot guides on the housing 8. A guide groove 50, starting from the proximal end of the outer side 24 of the housing 8, extends obliquely to the distal end of the outer side 26 of the housing 8. The guide groove 50 is formed on two outer sides 48 of the housing 8 which are aligned normally to the longitudinal slot 42 of the tube 36, for forming these slot guides. One of the projections 46 is engaged in each of the two guide grooves 50. If the tube 36 is displaced by way of a suitable actuation of the slider 38 in the distal direction, then the engagement of the projections 46 which are formed on the tube 36 into the obliquely aligned guide grooves 50 of the housing 8 has the effect of the housing 8 being moved from a position, in which the picture sensor 14 and the light diodes 18 are arranged within the inner lumen 22 of the hollow shank 2, into a position, in which the picture sensor 14 and the light diodes 18 are arranged outside the inner lumen 22 of the hollow shank. The housing 8 is then retracted back into the hollow shank 2 given a displacement of the tube 36 in the proximal direction.

While specific embodiments of the invention have been shown and described in detail to illustrate the application of the principles of the invention, it will be understood that the invention may be embodied otherwise without departing from such principles.

The invention claimed is:

1. A shank instrument comprising:
   a hollow shank;
   at least one housing integrated in the hollow shank at a distal side thereof; and
   at least one electronic picture sensor arranged in the at least one housing for optically capturing a region which is located distally from the hollow shank or a light source located in the at least one housing for illuminating a region which is located distally from the hollow shank or both at least one electronic picture sensor arranged in the at least one housing for optically capturing a region which is located distally from the hollow shank and a light source located in the at least one housing for illuminating the region; and
   at least one elongate carrier which is guided in the hollow shank, wherein:
   the housing is movable in a straight-lined course from a position, in which the picture sensor or the light source or both the picture sensor and the light source are arranged within the inner lumen of the hollow shank, into a position, in which the picture sensor or the light source or both the picture sensor and the light source are arranged outside the inner lumen of the hollow shank;
   the housing is displaceable through an opening which is formed on the peripheral wall of the hollow shank;
   the housing is supported, at a housing inner-lying outer side which is opposite and away from the opening on the at least one elongate carrier which is guided in the hollow shank;
   the at least one elongate carrier is configured elastically resiliently transverse to longitudinal extensions of the at least one elongate carrier;
   the at least one elongate carrier extends essentially over a whole length of the hollow shank and is fixed in a region of a proximal end of the hollow shank or at a proximal side of the hollow shank;
   the at least one elongate carrier is formed by a flat tube;

the housing is movably coupled with a push-pull element;
the push-pull element is movable in the hollow shank in the longitudinal direction of the hollow shank;
the push-pull element comprises at least one projection extending transverse to a push-pull element movement direction;
the at least one projection extends into a guide groove formed on an outer side of the housing;
the guide groove is oriented obliquely in the radial direction.

2. A shank instrument according to claim 1, wherein an outer-lying outer side of the housing is aligned in a flush manner with an outer side of the peripheral wall of the hollow shank in a position of the housing within the inner lumen of the hollow shank.

3. A shank instrument according to claim 1, wherein a recess which runs in the longitudinal direction of the hollow shank and into which the at least one elongate carrier engages is formed on the outer side of the housing which is away from the opening which is formed on the peripheral wall of the hollow shank.

4. A shank instrument according to claim 1, further comprising connection leads which are connected to the picture sensor or to the light source or to both the picture sensor and the light source are led through the flat tube to the proximal side of the hollow shank.

5. A shank instrument according to claim 1, wherein the push-pull element is formed by another tube with a longitudinal slot which is formed thereon, wherein the housing engages into the longitudinal slot and projections engage into guide grooves, the guide grooves being formed in two outer sides of the housing which are away from one another, the projections being formed on the two longitudinal sides of the longitudinal slot.

6. A shank instrument according to claim 2, wherein a recess, which runs in the longitudinal direction of the hollow shank and into which the at least one elongate carrier engages, is formed on the outer side of the housing which is away from the opening.

7. A shank instrument comprising:
a hollow shank;
at least one housing integrated in the hollow shank at a distal side thereof; and
at least one electronic picture sensor arranged in the at least one housing for optically capturing a region which is located distally from the hollow shank or a light source located in the at least one housing for illuminating a region which is located distally from the hollow shank or both at least one electronic picture sensor arranged in the at least one housing for optically capturing a region which is located distally from the hollow shank and a light source located in the at least one housing for illuminating the region; and
at least one elongate carrier which is guided in the hollow shank, wherein:
the housing is movable in a straight-lined course from a position, in which the picture sensor or the light source or both the picture sensor and the light source are arranged within the inner lumen of the hollow shank, into a position, in which the picture sensor or the light source or both the picture sensor and the light source are arranged outside the inner lumen of the hollow shank;
the housing is displaceable through an opening which is formed on the peripheral wall of the hollow shank;
the housing is supported, at a housing inner-lying outer side which is opposite and away from the opening on the at least one elongate carrier which is guided in the hollow shank;
the at least one elongate carrier is configured elastically resiliently transverse to longitudinal extensions of the at least one elongate carrier;
the at least one elongate carrier extends essentially over a whole length of the hollow shank and is fixed in a region of a proximal end of the hollow shank or at a proximal side of the hollow shank;
the housing movably coupled with a push-pull element which is movable in the hollow shank in the longitudinal direction of the hollow shank; and
the push-pull element comprises at least one projection which is aligned transversely to a push-pull element movement direction and engages into a guide groove which is formed on an outer side of the housing and runs obliquely in the radial direction.

8. A shank instrument according to claim 7, wherein the push-pull element is formed by a tube with a longitudinal slot which is formed thereon, wherein the housing engages into the longitudinal slot and projections engage into guide grooves, the guide grooves being formed in two outer sides of the housing which are away from one another, the projections being formed on the two longitudinal sides of the longitudinal slot.

9. A shank instrument comprising:
a hollow shank;
at least one housing integrated in the hollow shank at a distal side thereof; and
at least one electronic picture sensor arranged in the at least one housing for optically capturing a region which is located distally from the hollow shank or a light source located in the at least one housing for illuminating a region which is located distally from the hollow shank or both at least one electronic picture sensor arranged in the at least one housing for optically capturing a region Which is located distally from the hollow shank and a light source located in the at least one housing for illuminating the region; and
at least one elongate carrier which is guided in the hollow shank, wherein:
the housing is movable in a straight-lined course from a position, in which the picture sensor or the light source or both the picture sensor and the light source are arranged within the inner lumen of the hollow shank, into a position, in which the picture sensor or the light source or both the picture sensor and the light source are arranged outside the inner lumen of the hollow shank;
the housing is displaceable through an opening which is formed on the peripheral wall of the hollow shank;
the housing is supported, at a housing inner-lying outer side which is opposite and away from the opening on the at least one elongate carrier which is guided in the hollow shank;
the at least one elongate carrier is configured elastically resiliently transverse to longitudinal extensions of the at least one elongate carrier;
the at least one elongate carrier extends essentially over a whole length of the hollow shank and is fixed in a region of a proximal end of the hollow shank or at a proximal side of the hollow shank;
the housing is movably coupled with a push-pull element which is movable in the hollow shank in the longitudinal direction of the hollow shank;

the push-pull element is formed by a tube with a longitudinal slot which is formed thereon;

the housing engages into the longitudinal slot and projections engage into guide grooves; the guide grooves are formed in two outer sides of the housing Which are away from one another;

the projections are formed on the two longitudinal sides of the longitudinal slot; and the guide grooves are oriented obliquely in a radial direction.

* * * * *